(12) United States Patent
Bar-Or et al.

(10) Patent No.: US 6,567,706 B2
(45) Date of Patent: May 20, 2003

(54) ELECTRODE FOR MUSCLE STIMULATION

(75) Inventors: Jonathan Bar-Or, Pardes Hana (IL); Giora Arbel, Kfar-Saba (IL)

(73) Assignee: N.E.S.S. Neuromuscular Electrical Stimulation Systems Ltd., Ra'anana (IL)

( * ) Notice: Subject to any disclaimer, the term of this patent is extended or adjusted under 35 U.S.C. 154(b) by 82 days.

(21) Appl. No.: 09/811,613

(22) Filed: Mar. 20, 2001

(65) Prior Publication Data

US 2001/0039444 A1 Nov. 8, 2001

(30) Foreign Application Priority Data

Mar. 20, 2000 (IL) ................................................. 135175

(51) Int. Cl.[7] ................................................. A61N 1/00
(52) U.S. Cl. ....................... 607/152; 607/149; 607/153; 600/391; 602/2
(58) Field of Search ................................. 607/152, 139, 607/140, 149, 153, 134; 600/391, 392, 395, 396, 397; 602/2, 5

(56) References Cited

U.S. PATENT DOCUMENTS

| | | | |
|---|---|---|---|
| 3,610,250 A | 10/1971 | Sarbacher | 128/379 |
| 4,445,518 A | 5/1984 | Eggli et al. | 128/783 |
| 4,699,146 A * | 10/1987 | Sieverding | 600/391 |
| 5,330,516 A * | 7/1994 | Nathan | 607/149 |
| 5,397,338 A * | 3/1995 | Grey et al. | 607/149 |
| 5,833,716 A | 11/1998 | Bar-Or et al. | 607/149 |
| 5,974,344 A * | 10/1999 | Shoemaker, II | 607/149 |
| 6,038,464 A * | 3/2000 | Axelgaard et al. | 600/391 |
| 6,212,435 B1 * | 4/2001 | Lattner et al. | 607/134 |
| 6,341,237 B1 * | 1/2002 | Hurtado | 607/152 |
| 6,438,428 B1 * | 8/2002 | Axelgaard et al. | 607/152 |
| 6,456,884 B1 * | 9/2002 | Kenney | 607/149 |

FOREIGN PATENT DOCUMENTS

| | | |
|---|---|---|
| GB | 2261290 A | 5/1993 |
| WO | WO98/53877 | 12/1998 |

* cited by examiner

Primary Examiner—Teresa Walberg
Assistant Examiner—Fadi H. Dahbour
(74) Attorney, Agent, or Firm—Jacobson Holman, PLLC

(57) ABSTRACT

The invention provides an electrode kit for muscle stimulation to be used in conjunction with a splint, the kit including an electrode carrier attachable to an interior surface of the splint and consisting of a relatively thin, flexible, tray-like member; a thin, flexible electrode member fixedly attached to the electrode carrier, and a skin-contacting pad member consisting of a piece of medium-absorptive material fixedly mounted on a rigidifying frame attachable to, and removable from, the electrode carrier.

8 Claims, 2 Drawing Sheets

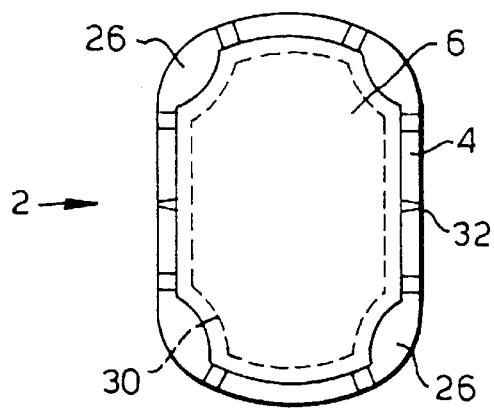
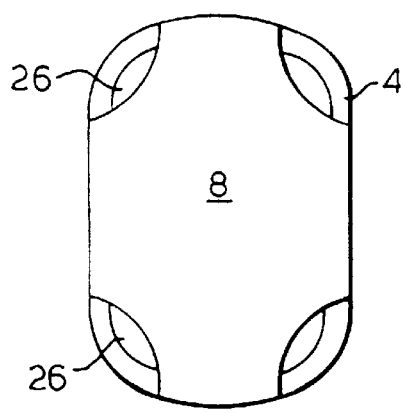
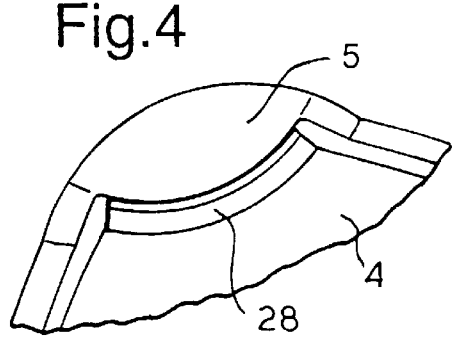
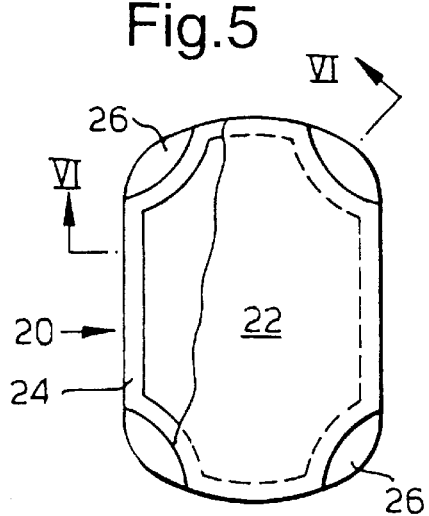
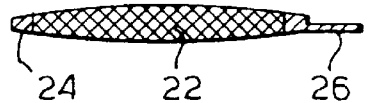

ELECTRODE FOR MUSCLE STIMULATION

FIELD OF THE INVENTION

The present invention relates to an electrode kit for muscle stimulation, to be used in conjunction with a splint.

Such splints are used for electrical stimulation of paralyzed limbs in therapeutic exercises (TES) and for generating limb function (FES).

BACKGROUND OF THE INVENTION

Electrodes for these devices usually comprise a base member attached to the inside of the splint and a pad consisting of a liquid-absorptive material, which constitutes the coupling agent between the electrode and the surface of the patient's skin. While the location of the electrodes relative to the motor points of the muscles to be stimulated is permanent and is determined by a clinician, the pads must be of a design facilitating rapid and easy removal and replacement; such replacement should require the use of no more than one hand.

In many of the known TES and FES devices, replacement of dried-out pads is a process complex enough to make it difficult for a patient having only one functional arm and hand to perform this operation himself and requires the aid of an assistant. Also, the location of the pad relative to the electrode is not always well-defined, producing a misalignment between the electrode and motor point which is liable to cause an undesirable overflow of the electrical stimulus.

DISCLOSURE OF THE INVENTION

It is thus one of the objects of the present invention to provide an electrode kit that not only facilitates easy removal and replacement of the pads, but also ensures exact reproducibility of the pad position relative to the motor point.

According to the invention, the above object is achieved by providing an electrode kit for muscle stimulation to be used in conjunction with a splint, said kit comprising an electrode carrier attachable to an interior surface of said splint and consisting of a relatively thin, flexible, tray-like member; a thin, flexible electrode member fixedly attached to said electrode carrier, and a skin-contacting pad member consisting of a piece of liquid-absorptive material fixedly mounted on a rigidifying frame attachable to, and removable from, said electrode carrier.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an exploded view of the electrode kit according to the present invention;

FIG. 2 is a top view of the electrode unit;

FIG. 3 illustrates the rear side of the unit shown in FIG. 2;

FIG. 4 is a greatly enlarged, perspective view of a corner of the electrode carrier;

FIG. 5 is a top view of the pad unit, and

FIG. 6 is a cross-sectional view along plane VI—VI of FIG. 5.

DETAILED DESCRIPTION OF PREFERRED EMBODIMENTS

Figure 1:
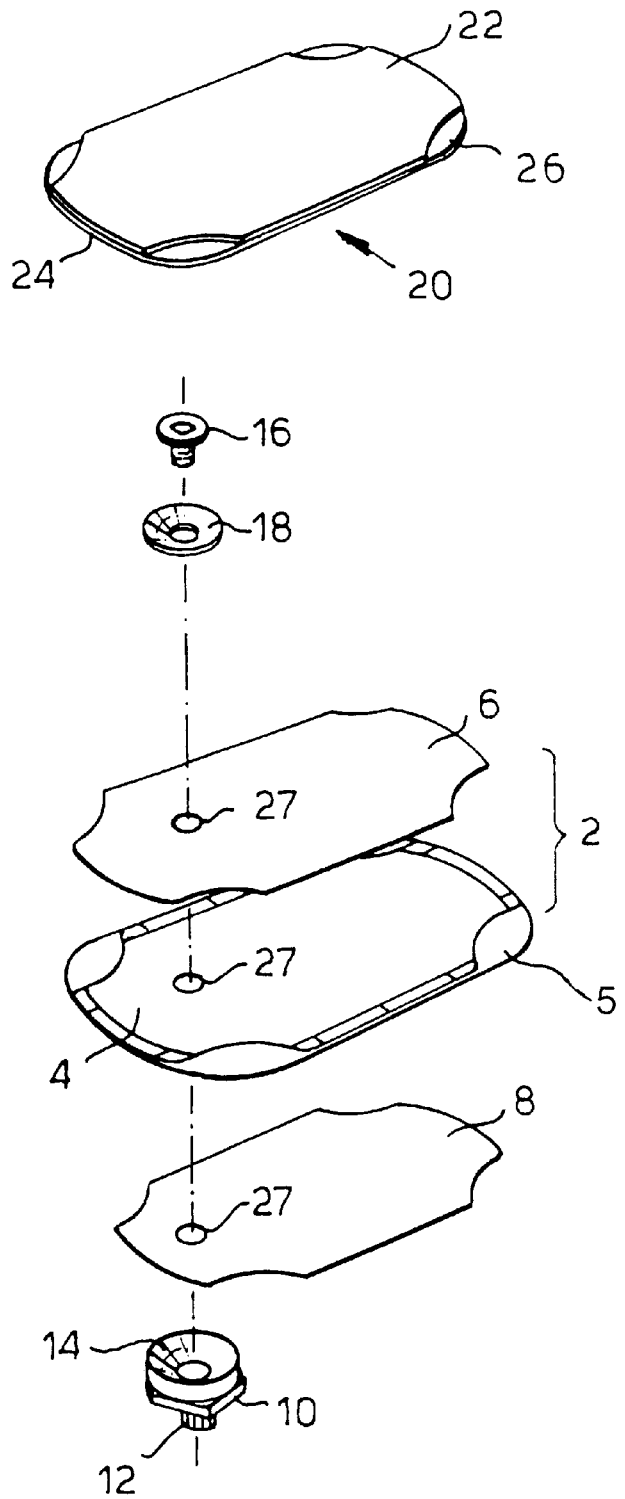

Referring now to the drawings, there is seen in the exploded view of FIG. 1 an electrode unit 2, comprised of a tray-like electrode carrier 4 having corner flaps 5, the electrode proper 6, and a double-faced, adhesive patch 8, used for attaching electrode carrier 4 to the splint (now shown). As will be described further below, electrode 6 is fixedly attached to carrier 4. Also seen is a metallic adapter 10 having a threaded projection 12 whereby it is mounted on the internal surface of the splint, and a conically countersunk threaded hole 14. Electrode unit 2 is clamped down onto the splint surface by means of a countersunk screw 16 and a conical washer 18. Adapter 10 also serves as the connecting terminal for the stimulating current. Obviously, electrode unit 2 must be flexible enough to adapt itself to the curved surface of the splint.

Further seen is the pad unit 20, comprised of pad 22 and a rigidifying, pad-carrying frame 24 having four corner tabs 26. A more detailed description of components 4–24 is given further below. Holes 27 are punched after the mounting of electrode unit 2.

FIG. 2 shows the electrode unit 2, comprised of carrier 4 and electrode 6. Carrier 4 has a tray-like shape, best seen in FIG. 1, and four corner flaps 5 which, as seen in FIG. 4, are offset relative to the surface of carrier 4, leaving open narrow slits 28. As explained further below, flaps 5 serve to retain, yet permit easy removal of, pad until 20.

Electrode 6 is made of a fine stainless-steel wire mesh and is attached to carrier 4 by ultrasonic welding. A preferred pattern of welding seams is indicated by dashed lines 30. Also seen are two oppositely located, arrowhead-like marks 32, which are instrumental in the accurate positioning of electrode unit 2 inside the splint.

Electrode carrier 4 is advantageously a plastic molding, using a mixture of polypropylene and polyvinyl. The rear side of carrier 4 is seen in FIG. 3, showing the adhesive patch 8 which comes already mounted on carrier 4.

FIG. 5 represents pad unit 20. Seen is frame 24 with its four corner tabs 26 which, as is shown in FIG. 6, are of a reduced thickness compared to the other parts of frame 24. It is these tabs 26 that are slipped into the respective slots 28 (FIG. 4) for mounting pad unit 20 on electrode unit 2.

Pad 22 is advantageously made of non-woven viscose, which is absorptive of liquids, gels, etc., and provides an effective conductive medium. Using a special mold, frame 24 is injection-molded right into the pre-cut viscose pad. In order to prevent fuzzing, the pad surface that will contact the patient's skin is impregnated with a synthetic rubber solution which binds the fibers together, without reducing their absorptivity to any significant degree.

Due to the unique method of connecting pad unit 20 to electrode carrier 4, pad unit 20 is easily and rapidly removed and replaced, using one hand only.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An electrode kit for muscle stimulation to be used in conjunction with a splint, said kit comprising:
    an electrode carrier consisting of a relatively thin, flexible, tray-like member having holding means, said carrier being attachable to an interior surface of said splint;
    a thin, flexible electrode member fixedly attached to said electrode carrier, and
    a skin-contacting pad member consisting of a piece of medium-absorptive material fixedly mounted on a rigidifying frame attachable to, and removable from, said holding means of the electrode carrier.

2. The electrode kit as claimed in claim 1, wherein said holding means is a plurality of slits into which said tab means can be slid and from which they can be withdrawn.

3. The electrode kit as claimed in claim 1, wherein said tab means are integral parts of the rigidifying frame of said pad member.

4. The electrode kit as claimed in claim 1, wherein said electrode carrier is attached to the interior surface of said splint by means of a double-sided adhesive patch.

5. The electrode kit as claimed in claim 1, wherein said flexible electrode member is made of a stainless-steel wire mesh attached to said tray-like member by ultrasonic welding.

6. The electrode kit as claimed in claim 1, wherein said medium-absorptive material is viscose.

7. The electrode kit as claimed in claim 1, wherein the skin-contacting surface of said pad member is impregnated with a synthetic rubber solution to prevent said surface from fuzzing.

8. The electrode kit as claimed in claim 1, wherein said holding means are engageable by tab means.

* * * * *